United States Patent
Crystal et al.

(10) Patent No.: US 7,368,553 B2
(45) Date of Patent: May 6, 2008

(54) ALTERNATIVELY SPLICED NUCLEIC ACID MOLECULES

(75) Inventors: Ronald G. Crystal, New York, NY (US); Neil R. Hackett, New York, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 350 days.

(21) Appl. No.: 10/971,643

(22) Filed: Oct. 21, 2004

(65) Prior Publication Data

US 2005/0153886 A1    Jul. 14, 2005

Related U.S. Application Data

(63) Continuation of application No. PCT/US03/12709, filed on Apr. 24, 2003.

(60) Provisional application No. 60/375,364, filed on Apr. 25, 2002.

(51) Int. Cl.
*C07H 21/04* (2006.01)
*C12P 21/06* (2006.01)
*C12N 15/00* (2006.01)
*C12N 5/00* (2006.01)
*C12N 15/74* (2006.01)

(52) U.S. Cl. ............... 536/23.5; 435/69.1; 435/252.3; 435/320.1; 435/325; 435/471

(58) Field of Classification Search ............... None
See application file for complete search history.

(56) References Cited

FOREIGN PATENT DOCUMENTS

WO    WO 94/01548    *    1/1994

OTHER PUBLICATIONS

Amano et al., "Alteration of splicing signals in a genomic/cDNA hybrid VEGF gene to modify the ratio of expressed VEGF isoforms enhances safety of angiogenic gene therapy," *Mol. Ther.*, 12 (4), 716-724 (Oct. 2005).
Whitlock et al., "Adenovirus-mediated transfer of a minigene expressing multiple isoforms of VEGF is more effective at inducing angiogenesis than comparable vectors expressing individual VEGF cDNAs," *Mol. Ther.*, 9 (1), 67-75 (Jan. 2004).
Williams, Database GenEmbl on LOCUS, Accession No. AL136131, "Direct Submission," Gene Sequence (Dec. 12, 2000).

* cited by examiner

*Primary Examiner*—Robert Landsman
(74) *Attorney, Agent, or Firm*—Leydig, Voit & Mayer, Ltd.

(57) ABSTRACT

The invention provides an isolated or purified nucleic acid molecule comprising SEQ ID NO:1, which contains cDNA comprising exons 1-5 of a vascular endothelial growth factor (VEGF) joined to genomic DNA comprising introns 5, 6, and 7 and exons 6, 7, and 8 of VEGF and a mutation in one or more of the splice donor, branch point, and splice acceptor regions, which promotes the production of a $VEGF_{189}$ isoform. Expression constructs, compositions, and cells comprising such a nucleic acid molecule also are provided by the invention.

8 Claims, 2 Drawing Sheets

```
ATGAACTTTCTGCTGTCTTGGGTGCATTGGAGCCTTGCCTTGCTGCTCTACCTCCACCATGCCAAGTGGTCC
CAGGCTGCACCCATGGCAGAAGGAGGAGGGCAGAATCATCACGAAGTGGTGAAGTTCATGGATGTCTATCAG
CGCAGCTACTGCCATCCAATCGAGACCCTGGTGGACATCTTCCAGGAGTACCCTGATGAGATCGAGTACATC
TTCAAGCCATCCTGTGTGCCCCTGATGCGATGCGGGGCTGCTGCAATGACGAGGGCCTGGAGTGTGTGCCC
ACTGAGGAGTCCAACATCACCATGCAGATTATGCGGATCAAACCTCACCAAGGCCAGCACATAGGAGAGATG
AGCTTCCTACAGCACAACAAATGTGAATGCAGACCAAAGAAAGATAGAGCTCGACAAGAAAAGTAAGTGGCC
CTGACTTTAGCACTTCTCCCTCTCCATGGCCGGTTGTCTTGGTTTGGGGCTCTTGGCTACCTCTGTTGGGGG
CTCCCATAGCCTCCCTGGGTCAGGGACTTGGTCTTGTGGGGACTTGTGGTGGCAGCAACAATGGGATGGAG
CCAACTCCAGGATGATGGCTCTAGGGCTAGTGAGAAAACATAGCCAGGAGCCTGGCACTTCCTTTGGAAGGG
ACAATGCCTTCTGGGTCTCCAGATCATTCCTGACCAGGACTTGCTGTTTCGGTGTGTCAGGGGGCACTGTGG
ACACTGGCTCACTGGCTTGCTCTAGGACACCCACAGTGGGGAGAGGGAGTGGGTGGCAGAGAGGCCAGCTTT
TGTGTGTCAGAGGAAATGGCCTCTTTTGGTGGCTGCTGTGACGGTGCAGTTGGATGCGAGGCCGGCTGGAGG
GTGGTTTCTCAGTGCATGCCCTCCTGTAGGCGGCAGGCGGCAGACACACAGCCCTCTTGGCCAGGGAGAAAA
AGTTGAATGTTGGTCATTTTCAGAGGCTTGTGAGTGCTCCGTGTTAAGGGGCAGGTAGGATGGGTGGGGGA
CAAGGTCTGGCGGCAGTAACCCTTCAAGACAGGGTGGGCGGCTGGCATCAGCAAGAGCTTGCAGGGAAAGAG
AGACTGAGAGAGAGCACCTGTGCCCTGCCCTTTCCCCCACACCATCTTGTCTGCCTCCAGTGCTGTGCGGAC
ATTGAAGCCCCCACCAGGCCTCAACCCCTTGCCTCTTCCCTCAGCTCCCAGCTTCCAGAGCGAGGGGATGCG
GAAACCTTCCTTCCACCCTTTGGTGCTTTCTCCTAAGGGGACAGACTTGCCCTCTCTGGTCCCTTCTCCCC
CTCCTTTCTTCCCTGTGACAGACATCCTGAGGTGTGTTCTCTTGGGCTTGGCAGGCATGGAGAGCTCTGGTT
CTCTTGAAGGGGACAGGCTACAGCCTGCCCCCCTTCCTGTTTCCCCAAATGACTGCTCTGCCATGGGGAGAG
TAGGGGGCTCGCCTGGGCTCGGAAGAGTGTCTGGTGAGATGGTGTAGCAGGCTTTGACAGGCTGGGGAGAGA
ACTCCCTGCCAAGTACCGCCCAAGCCTCTCCTCCCCAGACCTCCTTAACTCCCACCCCATCCTGCTGCCTGC
CCAGGGCTCCAGGACACCCAGCCCTGCCTCCCAGTCCAGGTCGTGCTGAGCAGGCTGGTGTTGCTCTTGGTT
CCGTGCCAGCTCCCAAGGTAGCCGCTTCCCCCACACCGGGATTCCCAGAGGTTCTGTCGCAGTTGCAAATGA
AGGCACAAGGCCTGATACACAGCCCTCCCTCCCACTCCTGCTCCCCATCCAGGCAGGTCTCTGACCTTCTCC
CCAAAGTCTGGCCTACCTTTTATCACCCCCGGACCTTCAGGGTCAGACTTGGACAGGGCTGCTGGGCAAAGA
GCCTTCCCTCAGGCTTTGCCCCCTGCCGGGGACTGGGAGCCACTGTGAGTGTGGAGACCTTTGGGTCCTGTG
CCCTCCACCCAGTCTCGGCTTCCCACCAAAGCCTTGTCAGGGGCTGGGTTTGCCATCCCATGGTGGGCAGCG
TGAGGAGAAGAAAGAGCCATCGAGTGCTTGCTGCCCAGACACGCCTGTGTGCGCCCGCGCATGCCTCCCCAG
AGACCACCTGCCTCCTGACACTTCCTCCGGGAAGCGGCCCTGTGTGGCTTTGCTTTGGTCGTTCCCCCATCC
CTGCCCACCTTACCACTTCACTGACTCCCCCCACCGCCCCGCTCTCTCTGTCTCTGTTTTTTTTTTTC
CAGAAAATCAGTTCGAGGAAAGGGAAAGGGGCAAAAACGAAAGCGCAAGAAATCTAGATATAAGTCCTGGAG
CGTGTAAGTTGGTGCCCGCTGCTGTCTAATGCCCTGGAGCCTCCCTGGCCCCCAGTACAACCTCCGCCTGCC
ATTCCCTGTAACCCTGCCTCCCTCCCCTGGTCCTTCCCTGGCTCTCATCCTCCTGGCCCGTGTCTCTCTCTC
ACTCTCTCACTCCACTAATTGGCACCAACGGGTAGATTTGGTGGTGGCATTGCTGGTCCAGGGTTGGGGTGA
ATGGGGGTGCCGACTTGGCCTGGAGGATTAAGGGAGGGGACCCTGGCTTGGCTGGGCACCGATTTTCTCTCA
CCCACTGGGCACTGGTGGCGGGCCCATGTTGGCACAGGTGCCTGCTCACCCAACTGGTTTCCATTGCTCTAG
GCTTCTGCACTCGTCTGGAAGCTGAGGGTGGTGGGGAGGGCAGACATGGCCCAAGAAGGGCTGTGAATGACT
GGAGGCAGCTTGCTGAATGACTCCTTGGCTGAAGGAGGAGCTTGGGTGGGATCAGACACCATGTGGCGGCCT
CCCTTCATCTGGTGGAAGTGCCCTGGCTCCTCACGGAGGTGGGGCCTCTGGAGGGGAGCCCCCTATTCCGGC
CCAACCCATGGCACCCACAGAGGCCTCCTTGCAGGGCAGCCTCTTCCTCTGGGTCGGAGGCTGTGGTGGGCC
CTGCCCTGGGCCCTCTGGCCACCAGCGGCCTGGCCTGGGGACACCGCCTCCGGGCTTAGCCTCCCATCACAC
CCTACTTTAGCCCACCTTGGTGGAAGGGCCTGGACATGAGCCTTGCACGGGGAGAAGGTGGCCCCTGATTGC
CATCCCCAGCAGGTGAAGAGTCAAGGCGTGCTCCGATGGGGGCAACAGCAGTTGGGTCCCTGTGGCCTGAGA
CTCACCCTTGTCTCCCAGAGACACAGCATTGCCCCTTATGGCAGCCTCTCCCTGCACTCTCTGCCCGTCTGT
GCCCGCCTCTTCCTGCGGCAGGTGTCCTAGCCAGTGCTGCCTCTTTCGCCGCTCTCTCTGTCTTTTGCTGT
AGCGCTCGGATCCTTCCAGGGCCTGGGGGCTGACCGGCTGGGTGGGGGTGCAGCTGCGGACATGTTAGGGGG
TGTTGCATGGTGATTTTTTTCTCTCTCTCTGCTGATGCTCTAGCTTAGATGTCTTTCCTTTTGCCTTTTTG
CAGTCCCTGTGGGCCTTGCTCAGAGCGGAGAAAGCATTTGTTTGTACAAGATCCGCAGTGTAAATGTTCCTG
CAAAAACACAGACTCGAGATGCAAGGCGAGGCAGCTTGAGTTAAACGAACGTACTTGCAGGTTGGTTCCCAG
AGGGCAAGCAAGTCAGAGAGGGGCATCACACAGAGATGGGGAGAGAGAGAGAGAGTGAGCGAGCGA
GCGAGCGGGAGAGCGCCTGAGAGGGGCCAGCTGCTTGCTCAGTTTCTAGCTGCCTGAGATCTGCGAAGGGCG
AATTCCAGCACACTGGCGCCGTTACTAGTGGATCTGCCCACTCTCTTCCCCACACCAGCCCCTAGAGACTG
AACTGAAAACCCTCCTCAGCAGGGAGCCTCTTCTGATTAACTTCATCCAGCTCTGGTCACCCATCAGCTCTT
AAAATGTCAAGTGGGGACTGTTCTTTGGTATCCGTTCATTTGTTGCTTTGTAAAGTGTTCCCATGTCCTTGT
CTTGTCTCAAGTAGATTGCAAGCTCAGGAGGGTAGACTGGGAGCCCCTGAGTGGAGCTGCTGCTCAGGCCGG
GGCTCCCTGAGGGCAGGGCTGGGCTGTTCTCATACTGGGGCTTTCTGCCCCAGGACCACACCTTCCTGTCC
TCTCTGCTCTTATGGTGCCGGAGGCTGCAGTGACCCAGGGGCCCCCAGGAATGGGGAGGCCGCCTGCCTCAT
CGCCAGGCCTCCTCACTTGGCCCTAACCCCAGCCTTTGTTTTCCATTTCCCTCAGATGTGACAAGCCGAGGC
GGTGAAAGCTT [SEQ ID NO:1]
```

FIG. 1

MNFLLSWVHWSLALLLYLHHAKWSQAAPMAEGGGQNHHEVVKFMDVYQRSYCHPIET
LVDIFQEYPDEIEYIFKPSCVPLMRCGGCCNDEGLECVPTEESNITMQIMRIKPHQG
QHIGEMSFLQHNKCECRPKKDRARQEKKSVRGKGKGQKRKRKKSRYKSWSVYVGARC
CLMPWSLPGPHPCGPCSERRKHLFVQDPQTCKCSCKNTDSRCKARQLELNERTCRCD
KPRR [SEQ ID NO:2]

FIG. 2

Consensus Splice Donor Site
    Exon....AG/GTAAGT [SEQ ID NO:3]

Consensus Branch Point
    Intron...YNYTRAC..Splice Acceptor Site [SEQ ID NO:4]

Consensus Splice Acceptor Site
    Branch Point..YYYYYYYYYYYYYNCAG/G..Exon [SEQ ID NO:5]

Y can be a C or a T
R can be a G or an A
N can be an A, C, G, or a T

FIG. 3

SEQUENCE LISTING

```
<160> NUMBER OF SEQ ID NOS: 15

<210> SEQ ID NO 1
<211> LENGTH: 4259
<212> TYPE: DNA
<213> ORGANISM: Artificial
<220> FEATURE:
<223> OTHER INFORMATION: Synthetic

<400> SEQUENCE: 1
atgaactttc tgctgtcttg ggtgcattgg agccttgcct tgctgctcta cctccaccat      60
gccaagtggt cccaggctgc acccatggca gaaggaggag ggcagaatca tcacgaagtg     120
gtgaagttca tggatgtcta tcagcgcagc tactgccatc caatcgagac cctggtggac     180
atcttccagg agtaccctga tgagatcgag tacatcttca gccatcctg tgtgccctg      240 atgcgatgcg ggggctgctg caatgacgag ggcctggagt gtgtgccac tgaggagtcc     300 aacatcacca tgcagattat gcggatcaaa cctcaccaag gccagcacat aggagagatg     360
agcttcctac agcacaacaa atgtgaatgc agaccaaaga aagatagagc tcgacaagaa     420
```

```
aagtaagtgg ccctgacttt agcacttctc cctctccatg gccggttgtc ttggtttggg    480
gctcttggct acctctgttg ggggctccca tagcctccct gggtcaggga cttggtcttg    540 tggggggactt gtggtggcag caacaatggg atggagccaa ctccaggatg atggctctag    600
ggctagtgag aaaacatagc caggagcctg gcacttcctt tggaagggac aatgccttct    660
gggtctccag atcattcctg accaggactt gctgtttcgg tgtgtcaggg ggcactgtgg    720
acactggctc actggcttgc tctaggacac ccacagtggg gagagggagt gggtggcaga    780
gaggccagct tttgtgtgtc agaggaaatg gcctcttttg gtggctgctg tgacggtgca    840
gttggatgcg aggccggctg gagggtggtt tctcagtgca tgccctcctg taggcggcag    900
gcggcagaca cacagccctc ttggccaggg agaaaaagtt gaatgttggt cattttcaga    960
ggcttgtgag tgctccgtgt taaggggcag gtaggatggg gtgggggaca aggtctggcg   1020
gcagtaaccc ttcaagacag ggtgggcggc tggcatcagc aagagcttgc agggaaagag   1080
agactgagag agagcacctg tgccctgccc tttcccccac accatcttgt ctgcctccag   1140
tgctgtgcgg acattgaagc ccccaccagg cctcaacccc ttgcctcttc cctcagctcc   1200
cagcttccag agcgagggga tgcggaaacc ttccttccac cctttggtgc tttctcctaa   1260
gggggacaga cttgccctct ctggtccctt ctcccctcc tttcttccct gtgacagaca   1320
tcctgaggtg tgttctcttg ggcttggcag gcatggagag ctctggttct cttgaagggg   1380
acaggctaca gcctgccccc cttcctgttt ccccaaatga ctgctctgcc atggggagag   1440 taggggggctc gcctgggctc ggaagagtgt ctggtgagat ggtgtagcag ctttgacag   1500 gctgggagaa gaactccctg ccaagtaccg cccagcctc tcctcccag acctccttaa   1560 ctcccacccc atcctgctgc ctgcccaggg ctccaggaca cccagccctg cctcccagtc   1620
caggtcgtgc tgagcaggct ggtgttgctc ttggttccgt gccagctccc aaggtagccg   1680
cttcccccac accgggattc ccagaggttc tgtcgcagtt gcaaatgaag gcacaaggcc   1740
tgatacacag ccctccctcc cactcctgct ccccatccag gcaggtctct gaccttctcc   1800
ccaaagtctg gcctaccttt tatcaccccc ggaccttcag ggtcagactt ggacagggct   1860
gctgggcaaa gagccttccc tcaggctttg cccctgccg gggactggga gccactgtga   1920
gtgtggagac ctttgggtcc tgtgccctcc acccagtctc ggcttcccac caaagccttg   1980
tcaggggctg ggtttgccat cccatggtgg gcagcgtgag gagaagaaag agccatcgag   2040
tgcttgctgc ccagacacgc ctgtgtgcgc ccgcgcatgc ctcccagag accacctgcc   2100 tcctgacact tcctccggga agcggccctg tgtggctttg cttttggtcgt tcccccatcc   2160 ctgcccacct taccacttca ctgactcccc ccaccgcccc cgctctctct ctgtctctgt   2220
tttttttttt tccagaaaat cagttcgagg aaagggaaag gggcaaaaac gaaagcgcaa   2280
gaaatctaga tataagtcct ggagcgtgta agttggtgcc cgctgctgtc taatgccctg   2340
gagcctccct ggcccccagt acaacctccg cctgccattc cctgtaaccc tgcctccctc   2400
ccctggtcct tccctggctc tcatcctcct ggcccgtgtc tctctctcac tctctcactc   2460
cactaattgg caccaacggg tagatttggt ggtggcattg ctggtccagg gttggggtga   2520 atggggggtgc cgacttggcc tggaggatta agggaggggga ccctggcttg gctgggcacc   2580
gattttctct cacccactgg gcactggtgg cgggcccatg ttggcacagg tgcctgctca   2640
cccaactggt ttccattgct ctaggcttct gcactcgtct ggaagctgag ggtggtgggg   2700
agggcagaca tggcccaaga agggctgtga atgactggag gcagcttgct gaatgactcc   2760
```

-continued

```
ttggctgaag gaggagcttg ggtgggatca gacaccatgt ggcggcctcc cttcatctgg   2820
tggaagtgcc ctggctcctc acggaggtgg ggcctctgga ggggagcccc ctattccggc   2880
ccaacccatg gcaccacag aggcctcctt gcagggcagc ctcttcctct gggtcggagg    2940
ctgtggtggg ccctgccctg ggccctctgg ccaccagcgg cctggcctgg ggacaccgcc   3000
tccgggctta gctcccatc acaccctact ttagcccacc ttggtggaag ggcctggaca    3060
tgagccttgc acggggagaa ggtggcccct gattgccatc cccagcaggt gaagagtcaa   3120
ggcgtgctcc gatgggggca acagcagttg gtccctgtg gcctgagact caccccttgtc   3180 tcccagagac acagcattgc cccttatggc agcctctccc tgcactctct gcccgtctgt   3240
gcccgcctct tcctgcggca ggtgtcctag ccagtgctgc ctctttccgc cgctctctct   3300
gtcttttgct gtagcgctcg gatccttcca gggcctgggg gctgaccggc tgggtggggg   3360
tgcagctgcg gacatgttag ggggtgttgc atggtgattt ttttctctc tctctgctga    3420 tgctctagct tagatgtctt tccttttgcc ttttttgcagt ccctgtgggc cttgctcaga   3480
gcggagaaag catttgtttg tacaagatcc gcagtgtaaa tgttcctgca aaaacacaga   3540
ctcgagatgc aaggcgaggc agcttgagtt aaacgaacgt acttgcaggt tggttcccag   3600
agggcaagca agtcagagag gggcatcaca cagagatggg gagagagaga gagaaagaga   3660
gtgagcgagc gagcgagcgg gagagcgcct gagagggggcc agctgcttgc tcagtttcta   3720
gctgcctgag atctgcgaag ggcgaattcc agcacactgg cggccgttac tagtggatct   3780
gcccactctc ttccccacac cagccccctag agactgaact gaaaaccctc ctcagcaggg   3840
agcctcttct gattaacttc atccagctct ggtcacccat cagctcttaa aatgtcaagt   3900
ggggactgtt ctttggtatc cgttcatttg ttgctttgta aagtgttccc atgtccttgt    3960
cttgtctcaa gtagattgca agctcaggag ggtagactgg gagccctga gtggagctgc    4020 tgctcaggcc ggggctccct gagggcaggg ctggggctgt tctcatactg ggctttctg    4080 ccccaggacc acaccttcct gtcctctctg ctcttatggt gccggaggct gcagtgaccc   4140
aggggccccc aggaatgggg aggccgcctg cctcatcgcc aggcctcctc acttggccct   4200
aaccccagcc tttgttttcc atttccctca gatgtgacaa gccgaggcgg tgaaagctt    4259
```

<210> SEQ ID NO 2
<211> LENGTH: 232
<212> TYPE: PRT
<213> ORGANISM: Artificial
<220> FEATURE:
<223> OTHER INFORMATION: Synthetic

<400> SEQUENCE: 2

```
Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
```

-continued

```
                    100                 105                 110
Gln Gly Gln His Ile Gly Glu Met Ser Phe Leu Gln His Asn Lys Cys
        115                 120                 125
Glu Cys Arg Pro Lys Lys Asp Arg Ala Arg Gln Glu Lys Lys Ser Val
    130                 135                 140
Arg Gly Lys Gly Lys Gly Gln Lys Arg Lys Arg Lys Lys Ser Arg Tyr
145                 150                 155                 160
Lys Ser Trp Ser Val Tyr Val Gly Ala Arg Cys Cys Leu Met Pro Trp
                165                 170                 175
Ser Leu Pro Gly Pro His Pro Cys Gly Pro Cys Ser Glu Arg Arg Lys
            180                 185                 190
His Leu Phe Val Gln Asp Pro Gln Thr Cys Lys Cys Ser Cys Lys Asn
        195                 200                 205
Thr Asp Ser Arg Cys Lys Ala Arg Gln Leu Glu Leu Asn Glu Arg Thr
    210                 215                 220
Cys Arg Cys Asp Lys Pro Arg Arg
225                 230

<210> SEQ ID NO 3
<211> LENGTH: 8
<212> TYPE: DNA
<213> ORGANISM: Artificial
<220> FEATURE:
<223> OTHER INFORMATION: Synthetic

<400> SEQUENCE: 3 aggtaagt                                                                   8

<210> SEQ ID NO 4
<211> LENGTH: 7
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (2)..(2)
<223> OTHER INFORMATION: n can be a, c, g, or t

<400> SEQUENCE: 4 ynytrac                                                                    7

<210> SEQ ID NO 5
<211> LENGTH: 18
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (14)..(14)
<223> OTHER INFORMATION: n can be a, c, g, or t

<400> SEQUENCE: 5 yyyyyyyyy yyyncagg                                                        18

<210> SEQ ID NO 6
<211> LENGTH: 7
<212> TYPE: DNA
<213> ORGANISM: Artificial
<220> FEATURE:
<223> OTHER INFORMATION: Synthetic

<400> SEQUENCE: 6
```

```
cttttac                                                              7

<210> SEQ ID NO 7
<211> LENGTH: 7
<212> TYPE: DNA
<213> ORGANISM: Artificial
<220> FEATURE:
<223> OTHER INFORMATION: Synthetic

<400> SEQUENCE: 7 cactgac                                                              7

<210> SEQ ID NO 8
<211> LENGTH: 20
<212> TYPE: DNA
<213> ORGANISM: Artificial
<220> FEATURE:
<223> OTHER INFORMATION: Synthetic

<400> SEQUENCE: 8
gtttttttat tttccagaaa                                               20

<210> SEQ ID NO 9
<211> LENGTH: 20
<212> TYPE: DNA
<213> ORGANISM: Artificial
<220> FEATURE:
<223> OTHER INFORMATION: Synthetic

<400> SEQUENCE: 9
gttttttttt tttccagaaa                                               20

<210> SEQ ID NO 10
<211> LENGTH: 8
<212> TYPE: DNA
<213> ORGANISM: Artificial
<220> FEATURE:
<223> OTHER INFORMATION: Synthetic

<400> SEQUENCE: 10 gtgtacgt                                                             8

<210> SEQ ID NO 11
<211> LENGTH: 8
<212> TYPE: DNA
<213> ORGANISM: Artificial
<220> FEATURE:
<223> OTHER INFORMATION: Synthetic

<400> SEQUENCE: 11 gtgtaagt                                                             8

<210> SEQ ID NO 12
<211> LENGTH: 7
<212> TYPE: DNA
<213> ORGANISM: Artificial
<220> FEATURE:
<223> OTHER INFORMATION: Synthetic

<400> SEQUENCE: 12 accttac                                                              7

<210> SEQ ID NO 13
<211> LENGTH: 7
<212> TYPE: DNA
```

-continued

```
<213> ORGANISM: Artificial
<220> FEATURE:
<223> OTHER INFORMATION: Synthetic

<400> SEQUENCE: 13 ccctgag                                                                  7

<210> SEQ ID NO 14
<211> LENGTH: 16
<212> TYPE: DNA
<213> ORGANISM: Artificial
<220> FEATURE:
<223> OTHER INFORMATION: Synthetic

<400> SEQUENCE: 14
tttttatttc cagaaa                                                       16

<210> SEQ ID NO 15
<211> LENGTH: 16
<212> TYPE: DNA
<213> ORGANISM: Artificial
<220> FEATURE:
<223> OTHER INFORMATION: Synthetic

<400> SEQUENCE: 15
tttttctttc cagaaa                                                       16
```

ALTERNATIVELY SPLICED NUCLEIC ACID MOLECULES

CROSS-REFERENCE TO RELATED PATENT APPLICATIONS

This patent application is a continuation of International Patent Application No. PCT/US03/12709, filed Apr. 24, 2003, which designates the United States, and which claims the benefit of U.S. Provisional Patent Application No. 60/375,364, filed Apr. 25, 2002.

FIELD OF THE INVENTION

The invention pertains to an isolated or purified nucleic acid molecule consisting essentially of a nucleotide sequence comprising cDNA and genomic DNA, and its inclusion in an expression construct for use in gene therapy applications.

BACKGROUND OF THE INVENTION

Gene therapy is emerging as a popular form of treatment that aims to address a variety of disease states through the transfer of functional genetic material into cells. Conventionally, gene therapy is carried out by including a transgene composed of a cDNA or, less commonly, the genomic configuration of the transgene (including the exons and introns) into a gene delivery vehicle (e.g., a gene transfer vector). Typically, there is a limit to the amount of DNA or RNA (i.e., transgene) that can be packaged in a gene therapy vector. To minimize the size occupied by the transgene, expression cassettes containing the transgene generally contain cDNA rather than genomic clones. However, in some cases, gene therapy vectors have been constructed to contain introns. For example, a gene therapy vector useful in treating cystic fibrosis has been described which includes an intron-containing region in the 5' end of the primary transcript of the cystic fibrosis transmembrane conductance regulator (CFTR) gene. The intron-containing region in this vector is a hybrid between the cytomegalovirus (CMV) immediate early intron and an intron from the human immunoglobulin gene. The rationale for using an intron at the 5' end of the primary transcript is based on two considerations. First, in vitro transfection studies indicate that such genes introduced into cells are expressed more efficiently when the primary transcripts contain introns. Second, an intron at the 5' end of the primary transcript is convenient for PCR analyses to distinguish vector DNA from the mRNA transcript. Genomic clones have rarely been used in gene therapy with the exception of relatively small genomes (e.g., erythropoietin) or in the gutless adenovirus vectors for which a genomic clone of the human α1-antitrypsin gene has been used as a transgene. In vivo data using the gutless vector have shown prolonged expression of the transgene, but this observation was interpreted to reflect the properties of the gutless vector rather than the nature of the transgene. In contrast to cDNA, pre-mRNA splicing of genomic DNA is essential for protein production.

RNA splicing is part of a process whereby primary transcripts made by transcription of a DNA template by an RNA polymerase are rearranged to make messenger RNA (mRNA). For most mammalian genes, one or more introns present in the primary transcript are removed, leaving only the exons which, when spliced together, constitute the mature mRNA. The number and length of introns differ greatly among genes.

RNA splicing is mediated by the spliceosome, which is a large protein/RNA complex responsible for removing introns in a two-step process. First, cleavage occurs at the splice donor site (5' end of intron) exposing a 5'-phosphate, which immediately ligates to a 2'-OH at the branch point that is located close to the splice acceptor within the intron. Secondly, there is a cleavage at the splice acceptor site with the simultaneous ligation of the 3'-OH of the upstream exon to the 5'-phosphate of the downstream exon. These two steps result in the release of the intron as a lariat with a free 3'-OH end.

In the process of constitutive splicing, all of the introns are excised from the pre-mRNA to give a unique mRNA species. However, a number of genes have been described for which more than one mRNA species is derived from a single pre-mRNA. Such an occurrence is referred to as alternative splicing. When this takes place, many different isoforms of a protein can be produced from a pre-mRNA. Moreover, each of these isoforms can have different biological activities. An example of an alternatively spliced pre-mRNA transcript is demonstrated by the angiogenic factor VEGF. The VEGF-A (sometimes referred to as "VEGF-1") gene contains 8 exons and 7 introns that, by alternative splicing, can form at least six isoforms of the protein.

The longest protein isoform is VEGF206, whose mRNA contains the entirety of all eight exons encoding a pre-protein of 232 amino acids, which is processed to the mature form of 206 amino acids. Alternative splicing to produce the different isoforms is focused around exons 6, 7, and 8. The VEGF121 isoform results from joining the splice donor at the end of exon 5 directly to the splice acceptor in exon 8, thereby completely eliminating exons 6 and 7. Exon 6 is especially complex with three different potential splice donors which can ligate to exon 7, resulting in the VEGF206, VEGF189, and VEGF183 isoforms. The 3' non-translated end of the gene contains regulatory elements that increase mRNA half-life in response to ischemia. Since the mRNAs for all isoforms share the same 5' and 3' end, RT-PCR can be used to estimate the relative amounts in any tissue. In most normal tissues, VEGF165 and VEGF189 are most abundant, with changes in expression related to neoplastic transformation (see, e.g., Jackson et al., *J. Urol.*, 157, 2323-2328 (1997), and Cheung et al., *Hum. Pathol.*, 29, 910-914 (1998)). For example, in carcinomas originating in lung or colon, a switch to the shorter VEGF121 isoform was observed (see, e.g., Cheung et al. (1998), supra). In non-small cell lung cancer, an increase in VEGF189 has been associated with a more aggressive form of the disease, indicating a poor prognosis for the patient (see, e.g., Tokenaga et al., *Br. J. Cancer.*, 77, 998-1002 (1998)). In addition, the VEGF145 isoform was initially discovered in carcinomas (see, e.g., Poltorak et al., *J. Biol. Chem.*, 272, 7151-7158 (1997)) but has not been observed in non-transformed tissues (see, e.g., Jackson et al. (1997), supra, and Cheung et al. (1998), supra).

The significance of the VEGF isoforms is in their different biological activities. First, the different isoforms have different affinities for the VEGF receptors. At least three VEGF receptors (fltl, flkl/KDR, and neuropilin) are known, which are found in different cell types and at different times during development. Fltl mediates cell migration, while KDR is required for the proliferative effects of VEGF (see, e.g., Barleon et al., *Blood*, 87, 3336-3343 (1996)). While VEGF165 has approximately equal affinity to the flkl/KDR receptor and the fltl receptor, VEGF 121 has a much lower affinity for fltl and binds primarily to KDR (see, e.g., Keyt et al., *J. Biol. Chem,* 271, 7788-7795 (1996)). Thus, VEGF121 is expected to be biologically inactive in tissues lacking fltl. In the same way, neuropilin is believed to enhance the interaction of VEGF165 with KDR (but not fltl), but has no effect on the binding of VEGF121 to KDR (see, e.g., Gitay-Goren et al., *J. Biol. Chem.,* 271, 5519-5523 (1996), and Park et al., *J. Biol. Chem.,* 269, 25646-25654 (1994)). Second, the different VEGF isoforms differ in their ability to bind heparin and other negatively charged cell matrix components. VEGF121 is missing the basic domains located in exons 6 and 7 which determine interaction with heparin. The presence of heparin can modify both the affinity of the VEGF for its receptors and the residency time in tissue (see, e.g., Keyt et al. (1996), supra, and Cohen et al. (1995), supra). The heparin binding isoforms, such as VEGF165 and VEGF189, will bind extracellular matrix strongly and can be released as biologically active peptides by proteases such as plasmin (see, e.g., Keyt et al. (1996), supra, Athanassiades et al., *Bio. Reprod.,* 59, 643-654 (1998), and Terman et al., *Growth Factors,* 11, 187-195 (1994)).

The biological significance of the different properties of VEGF isoforms is proven by the phenotype of mice which are unable to make the heparin binding isoform VEGF164/188 (note that the mice VEGF isoforms are one amino acid shorter than the human homologues) (see, e.g., Carmeliet et al., *Nat. Med.,* 5, 495-502 (1999)). Complete deletion of only the VEGF gene is lethal to a mouse embryo even when only one of the two alleles is deleted (see, e.g., Carmeliet et al., *Nature,* 380, 435-439 (1996)). However, mice can be made with small genomic deletions which encompass exons 6 and 7, thereby making VEGF120 the only isoform that can be produced (see, e.g., Carmeliet et al. (1999), supra). Homozygote mice for VEGF120 are lethal neonatally and suffer from impaired myocardial angiogenesis, which results in decreased contractility and ischemic cardiomyopathy. Thus, the developmental roles of VEGF can be furnished by VEGF120 while the postnatal development of the blood supply, especially to cardiac muscle, depends on the VEGF164/VEGF188 isoforms. This evidence supports the contention that different therapeutic effects might be expected from the production of different isoforms or mixtures of isoforms of VEGF delivered by gene therapy. It is also conceivable that genes other than VEGF can be used in a similar manner. While alternative splicing can accomplish the production of different isoforms of a particular gene, it would be advantageous to construct nucleic acid molecules that comprise splice sites that promote the production of one isoform of a particular gene over another. Such nucleic acid molecules will allow for more control over splicing and isoform production and will be useful in therapeutic applications, as well as early, sensitive, and accurate methods for measuring the effectiveness of such therapeutic applications in a mammal.

The invention provides such nucleic acid molecules, therapeutic applications, and methods. These and other objects and advantages of the invention, as well as additional inventive features, will be apparent from the description of the invention provided herein.

BRIEF SUMMARY OF THE INVENTION

The invention provides an isolated or purified nucleic acid molecule consisting essentially of a nucleotide sequence of at least 1877 contiguous nucleotides of (a) SEQ ID NO:1 or (b) a nucleotide sequence encoding an angiogenic factor, wherein the nucleotide sequence comprises cDNA comprising exons 1-5 of a vascular endothelial growth factor (VEGF) joined to genomic DNA comprising introns 5, 6, and 7 and exons 6, 7, and 8 of VEGF, wherein the nucleotide sequence comprises a mutation in one or more of the splice donor, branch point, and splice acceptor regions contained in an exon selected from the group consisting of exons 5, 6, 7, and 8, wherein the mutation promotes the production of one isoform of VEGF as compared to another isoform of VEGF. Expression constructs, compositions, and cells comprising such a nucleic acid molecule also are provided by the invention.

BRIEF DESCRIPTION OF THE DRAWINGS

FIG. 1 sets forth the nucleotide sequence comprising cDNA and genomic DNA of a VEGF which promotes the production of VEGF189 at the expense of VEGF 165 [SEQ ID NO:1].

FIG. 2 sets forth the amino acid sequence corresponding to the protein encoded by the nucleotide sequence set forth in FIG. 1 [SEQ ID NO:2].

FIG. 3 sets forth the consensus nucleotide sequences of the splice donor, branch point, and splice acceptor sites of a nucleotide sequence encoding a VEGF [SEQ ID NO:3-5].

DETAILED DESCRIPTION OF THE INVENTION

The invention is predicated, at least in part, on the knowledge that different protein isoforms encoded by the same gene and produced by alternative splicing often have different functions, and the knowledge that the relative abundance of different mRNAs formed by alternative splicing is controlled by the sequences in the splice donor and slice acceptor sites in the intron sequences 3' and 5' to each exon. The invention provides an isolated or purified nucleic acid molecule consisting essentially, or even consists of, of a nucleotide sequence of at least 1877 contiguous nucleotides of SEQ ID NO:1. Preferably, such an isolated or purified nucleic acid molecule consists essentially of a nucleotide sequence encoding a gene capable of producing different isoforms of a protein, such as a vascular endothelial growth factor (VEGF). Also preferably, the nucleic acid molecule consists essentially of a nucleotide sequence comprising cDNA joined to genomic DNA. The invention also provides an isolated or purified nucleic acid molecule consisting essentially of a nucleotide sequence encoding an angiogenic factor comprising cDNA comprising exons 1-5 of a VEGF joined to genomic DNA comprising introns 5, 6, and 7 and exons 6, 7, and 8 of VEGF, wherein the nucleotide sequence comprises a mutation in one or more of the splice donor, branch point, and splice acceptor regions contained in an exon selected from the group consisting of exons 5, 6, 7, and 8, wherein the mutation promotes the production of one isoform of VEGF as compared to another isoform of VEGF. Preferably, the production of an isoform of VEGF that binds heparin will be promoted over the production of an isoform of VEGF that does not bind heparin. The invention further provides an isolated or purified nucleic acid molecule consisting of a nucleotide sequence of at least 1877 contiguous nucleotides of the aforementioned nucleotide sequence encoding an angiogenic factor comprising cDNA joined to genomic DNA.

By "isolated" is meant the removal of a nucleic acid molecule from its natural environment. By "purified" is meant that a given nucleic acid molecule, whether one that has been removed from nature or synthesized and/or amplified under laboratory conditions, has been increased in purity, wherein "purity" is a relative term, not "absolute purity." A "nucleic acid molecule" is intended to encompass a polymer of DNA or RNA (i.e., a polynucleotide), which can be single-stranded or double-stranded and which can contain non-natural or altered nucleotides.

While the isolated or purified nucleic acid molecule of the invention consists essentially of a nucleotide sequence of at least 1877 contiguous nucleotides, larger nucleic acid molecules also are contemplated. For example, the isolated or purified nucleic acid molecule of the invention can consist essentially of a nucleotide sequence of at least 1900 contiguous nucleotides, at least 1910 contiguous nucleotides, at least 1920 contiguous nucleotides, at least 1930 contiguous nucleotides, at least 1940 contiguous nucleotides, or even at least 1950 contiguous nucleotides of SEQ ID NO:1 or of the aforementioned nucleotide sequence encoding an angiogenic factor comprising cDNA joined to genomic DNA. Still larger nucleic acid molecules also are contemplated, such as isolated or purified nucleic acid molecules consisting essentially of a nucleotide sequence of at least 2000 contiguous nucleotides, at least 2225 contiguous nucleotides, at least 2500 contiguous nucleotides, or even at least 3000 contiguous nucleotides of SEQ ID NO:1 or of the aforementioned nucleotide sequence encoding an angiogenic factor comprising cDNA joined to genomic DNA. Generally, any size nucleic acid molecule is contemplated as long as the isolated or purified nucleic acid molecule consists essentially of contiguous nucleotides spanning 44% or more, 50% or more, or even 55% or more of SEQ ID NO:1 or of the aforementioned nucleotide sequence encoding an angiogenic factor comprising cDNA joined to genomic DNA.

When the nucleic acid molecule of the invention comprises both cDNA and genomic DNA sequences, these DNA sequences are joined to one another. In this respect, a cDNA is "joined" to genomic DNA when genomic DNA is included in the nucleic acid molecule and is positioned in the molecule either directly 5' or 3' to a cDNA sequence. When multiple genomic DNAs are included in the nucleic acid molecule, such sequences can be positioned either 5' and/or 3' to a cDNA sequence. The nucleic acid molecule is constructed such that the production of one isoform of a particular gene is promoted at the expense of another isoform. In such instances, the nucleotide sequence comprising the splice donor, branch point, and/or the splice acceptor site is manipulated (e.g., by site-specific mutagenesis) and, in effect, determines sites within the nucleic acid molecule which are to be removed by splicing. This allows for more control over which particular isoform is to be produced by alternative splicing.

Given the complexity and length of pre-mRNA, the mechanism by which splice sites are chosen is necessarily complicated. Two strategies have been used to evaluate the essential sequences for splicing: (1) the analysis of natural and induced mutations that modulate splicing efficiency and location, and (2) statistical studies of the sequences involved in splicing. These extensive studies can be summarized as indicating the nucleotide frequencies at the splice donor, branch point, and splice acceptor site. In the instance where the pre-mRNA encodes a VEGF, correspondence with the consensus splicing sequences shown in FIG. 3 is indicative of efficient splicing. Similarly, a discordance with the consensus sequence is indicative of inefficient splicing. Consensus splice sites in other genes can be determined through routine experimentation. Accordingly, the determination of splice sites as they pertain to VEGF are in no way limiting.

In analyzing splice site recognition, various mathematical assessments, such as the Senaphthy score, can be performed to assess the match of a splice site to the statistical consensus (see, e.g., Senaphthy et al., *Methods Enzymol.*, 183, 252-278 (1990)). Mutations that have a high impact on splicing efficiency have a high impact on the Senaphthy score, while polymorphisms (i.e., mutations with no effect on splicing) have a small impact. The value of Senaphthy scores, or other more complex scores (see, e.g., Stephens et al., *J. Mol. Biol.*, 228, 1124-1136 (1992)), is that they allow a prediction of the effect of a mutation on the efficiency of splicing. This information can be used to design splice donor and acceptor sites with greater and lesser efficiency to promote or suppress the usage of given splice sites.

The invention also provides a nucleic acid molecule consisting essentially of a nucleotide sequence that is complementary to a nucleotide sequence consisting essentially of at least 1877 contiguous nucleotides of SEQ ID NO:1. Such a complementary nucleotide sequence will hybridize under stringent conditions to a nucleic acid molecule consisting essentially of a nucleotide sequence of at least 1877 contiguous nucleotides of SEQ ID NO:1.

The phrase "hybridizes to" refers to the selective binding of a single-stranded nucleic acid probe to a single-stranded target DNA or RNA sequence of complementary sequence when the target sequence is present in a preparation of heterogeneous DNA and/or RNA. "Stringent conditions" are sequence-dependent and will be different in different circumstances. Generally, stringent conditions are selected to be about 20° C. lower than the thermal melting point (Tm) for the specific sequence at a defined ionic strength and pH. The Tm is the temperature (under defined ionic strength and pH) at which 50% of the target sequence hybridizes to a perfectly matched probe.

For example, under stringent conditions, as that term is understood by one skilled in the art, hybridization is preferably carried out using a standard hybridization buffer at a temperature ranging from about 50° C. to about 75° C., even more preferably from about 60° C. to about 70° C., and optimally from about 65° C. to about 68° C. Alternately, formamide can be included in the hybridization reaction, and the temperature of hybridization can be reduced to preferably from about 35° C. to about 45° C., even more preferably from about 40° C. to about 45° C., and optimally to about 42° C. Desirably, formamide is included in the hybridization reaction at a concentration of from about 30% to about 50%, preferably from about 35% to about 45%, and optimally at about 40%. Moreover, optionally, the hybridized sequences are washed (if necessary to reduce non-specific binding) under relatively highly stringent conditions, as that term is understood by those skilled in the art. For instance, desirably, the hybridized sequences are washed one or more times using a solution comprising salt and detergent, preferably at a temperature of from about 50° C. to about 75° C., even more preferably from about 60° C. to about 70° C., and optimally from about 65° C. to about 68° C. Preferably, a salt (e.g., such as sodium chloride) is included in the wash solution at a concentration of from about 0.01 M to about 1 M. Optimally, a detergent (e.g., such as sodium dodecyl sulfate) is also included at a concentration of from about 0.01% to about 1%.

In view of the above, "highly stringent conditions" preferably allow for about 25% to about 5% mismatch, more preferably about 15% to about 5% mismatch, and most preferably about 10% to about 5% mismatch. "Moderately stringent conditions" preferably allow for about 40% to about 15% mismatch, more preferably about 30% to about 15% mismatch, and most preferably about 20% to about 15% mismatch. "Low stringent conditions" preferably allow for about 60% to about 35% mismatch, more preferably about 50% to about 35% mismatch, and most preferably about 40% to about 35% mismatch. With respect to the preceding ranges of mismatch, 1% mismatch corresponds to one degree decrease in the melting temperature. It is generally appreciated that the stringent conditions can be manipulated by adjusting the concentration of formamide in the hybridization reaction. For example, conditions can be rendered more stringent by the addition of increasing amounts of formamide.

With respect to the aforementioned isolated or purified nucleic acid molecules, it is preferred that no insertions, deletions, inversions, and/or substitutions are present in the nucleic acid molecule. Such a nucleic acid molecule will code for a "wild-type" gene product (i.e., protein). However, it is suitable for the aforementioned isolated or purified nucleic acid molecules to comprise one or more insertions, deletions, inversions, and/or substitutions. Such a nucleic acid molecule will code for a "variant" gene product.

Preferably, the variant nucleic acid molecule will not differ functionally from the corresponding wild-type molecule. For example, any insertions, deletions, inversions, and/or substitutions contained within the nucleic acid molecule comprising a nucleotide sequence of at least 1877 contiguous nucleotides of SEQ ID NO:1 preferably will not (1) result in the introduction of a frame-shift mutation, (2) interfere with the ability of the promoter region to direct the transcription of the nucleotide sequence, or (3) interfere with the ability of the corresponding RNA transcript to be translated into a protein. In one embodiment, the one or more substitution(s) do(es) not result in a change in an amino acid encoded by the nucleic acid molecule. In an alternative embodiment, the one or more substitution(s) result(s) in the substitution of an amino acid with another amino acid of approximately equivalent size, shape, and/or charge.

Also with respect to the above, "will not differ functionally from" is intended to mean that the variant nucleic acid molecule will have activity characteristic of the wild-type molecule. However, the variant nucleic acid molecule can be more or less active than the wild-type molecule, as desired.

When desired, the nucleic acid molecule of the invention can be inserted into an expression construct. A nucleic acid molecule as described above can be cloned into any suitable expression construct and can be used to transform or transfect any suitable host. The selection of expression and methods to construct them are commonly known to persons of ordinary skill in the art and are described in general technical references (see, in general, "Recombinant DNA Part D," *Methods in Enzymology*, Vol. 153, Wu and Grossman, eds., Academic Press (1987)).

Suitable expression constructs include those designed for propagation and expansion or for expression or both. Examples of suitable expression constructs include plasmids, phagemids, cosmids, viruses, and other vehicles derived from viral or bacterial sources. Any of these expression constructs can be manipulated to include a nucleic acid sequence consisting essentially of at least 1877 contiguous nucleotides of SEQ ID NO:1 and can be prepared using standard recombinant DNA techniques described in, e.g., Sambrook et al., Molecular Cloning, a Laboratory Manual, 2d edition, Cold Spring Harbor Press, Cold Spring Harbor, N.Y. (1989), and Ausubel et al., Current Protocols in Molecular Biology, Greene Publishing Associates and John Wiley & Sons, New York, N.Y. (1994).

Plasmids are genetically engineered circular double-stranded DNA molecules and can be designed to contain an expression cassette comprising a nucleic acid molecule of the invention. Although plasmids were the first vector described for administration of therapeutic nucleic acids, the level of transfection efficiency is poor compared with other vectors. By complexing the plasmid with liposomes, the efficiency of gene transfer in general is improved. While the liposomes used for plasmid-mediated gene transfer strategies have various compositions, they are typically synthetic cationic lipids. Advantages of plasmid-liposome complexes include their ability to transfer large nucleic acid sequences and their relatively low immunogenicity. While plasmids are suitable for use in the invention, preferably the expression construct is a viral vector.

The viral vector can be any suitable viral vector. Suitable viral vectors include, but are not limited to, reoviruses, adenoviruses, adeno-associated viruses, papovaviruses, parvoviruses, picomaviruses, and enteroviruses of any suitable origin (preferably of animal origin (e.g., avian or mammalian) and desirably of human origin). Other suitable viral vectors are known in the art and are well characterized. Examples of such viral vectors are described in, for example, Fields et al., VIROLOGY Lippincott-Raven (3rd ed. (1996) and 4th ed. (2000)); ENCYCLOPEDIA OF VIROLOGY, R. G. Webster et al., eds., Academic Press (2nd ed., 1999); FUNDAMENTAL VIROLOGY, Fields et al., eds., Lippincott-Raven (3rd ed., 1995); Levine, "Viruses," Scientific American Library No. 37 (1992); MEDICAL VIROLOGY, D. O. White et al., eds., Academic Press (2nd ed. 1994); and INTRODUCTION TO MODERN VIROLOGY, Dimock, N. J. et al., eds., Blackwell Scientific Publications, Ltd. (1994). Preferably, the viral vector is derived from, or based on, a virus that normally infects animals, such as mammals (most preferably humans). Adenoviral (Ad) vectors based on human adenoviruses are preferred viral vectors.

Adenovirus is a 36 kb double-stranded DNA virus that efficiently transfers DNA in vivo to a variety of different target cell types. The Ad vector can be produced in high titers and can efficiently transfer DNA to replicating and non-replicating cells. The Ad vector genome can be generated using any species, strain, subtype, mixture of species, strains, or subtypes, or chimeric adenovirus as the source of vector DNA. Adenoviral stocks that can be employed as a source of adenovirus can be amplified from the adenoviral serotypes 1 through 51, which are currently available from the American Type Culture Collection (ATCC, Manassas, Va.), or from any other serotype of adenovirus available from any other source. For instance, an adenovirus can be of subgroup A (e.g., serotypes 12, 18, and 31), subgroup B (e.g., serotypes 3, 7, 11, 14, 16, 21, 34, and 35), subgroup C (e.g., serotypes 1, 2, 5, and 6), subgroup D (e.g., serotypes 8, 9, 10, 13, 15, 17, 19, 20, 22-30, 32, 33, 36-39, and 42-47), subgroup E (serotype 4), subgroup F (serotypes 40 and 41), or any other adenoviral serotype. Given that the human adenovirus serotype 5 (Ad5) genome has been completely sequenced, the adenoviral vector is described herein with respect to the Ad5 serotype. The Ad vector can be any adenoviral vector capable of growth in a cell, which is in some significant part (although not necessarily substantially) derived from or based upon the genome of an adenovirus. The Ad vector can be based on the genome of any suitable wild-type adenovirus. Preferably, the Ad vector is derived from the genome of a wild-type adenovirus of group C, especially of serotype 2 or 5. Ad vectors are well known in the art and are described in, for example, U.S. Pat. Nos. 5,559,099, 5,712,136, 5,731,190, 5,837,511, 5,846,782, 5,851,806, 5,962,311, 5,965,541, 5,981,225, 5,994,106, 6,020,191, and 6,113,913, International Patent Applications WO 95/34671, WO 97/21826, and WO 00/00628, and Thomas Shenk, "Adenoviridae and their Replication," and M. S. Horwitz, "Adenoviruses," Chapters 67 and 68, respectively, in *Virology*, B. N. Fields et al., eds., 3d ed., Raven Press, Ltd., New York (1996).

Preferably, the Ad vector is replication-deficient. By "replication-deficient" is meant that the Ad vector comprises a genome that lacks at least one replication-essential gene function. A deficiency in a gene, gene function, or gene or genomic region, as used herein, is defined as a deletion of sufficient genetic material of the viral genome to impair or obliterate the function of the gene whose nucleic acid sequence was deleted in whole or in part. Replication-essential gene functions are those gene functions that are required for replication (i.e., propagation) of a replication-deficient Ad vector. Replication-essential gene functions are encoded by, for example, the adenoviral early regions (e.g., the E1, E2, and E4 regions), late regions (e.g., the L1-L5 regions), genes involved in viral packaging (e.g., the IVa2 gene), and virus-associated RNAs (e.g., VA-RNA I and/or VA-RNA II). Preferably, the replication-deficient Ad vector comprises an adenoviral genome deficient in two or more gene functions required for viral replication. The two or more regions of the adenoviral genome are preferably selected from the group consisting of the E1, E2, and E4 regions. More preferably, the replication-deficient adenoviral vector comprises a deficiency in at least one replication-essential gene function of the E1 region (denoted an E1-deficient adenoviral vector). The E1 region of the adenoviral genome comprises the E1A region and the E1B region. The E1A and E1B regions comprise nucleic acid sequences coding for multiple peptides by virtue of RNA splicing. A deficiency of a gene function encoded by either or both of the E1A and/or E1B regions of the adenoviral genome (e.g., a peptide that performs a function required for replication) is considered a deficiency of a gene function of the E1 region in the context of the invention. In addition to such a deficiency in the E1 region, the recombinant adenovirus also can have a mutation in the major late promoter (MLP), as discussed in International Patent Application WO 00/00628. More preferably, the vector is deficient in at least one replication-essential gene function of the E1 region and at least part of the nonessential E3 region (e.g., an Xba I deletion of the E3 region) (denoted an E1/E3-deficient adenoviral vector).

Preferably, the adenoviral vector is "multiply deficient," meaning that the adenoviral vector is deficient in one or more gene functions required for viral replication in each of two or more regions of the adenoviral genome. For example, the aforementioned E1-deficient or E1/E3-deficient Ad vector can be further deficient in at least one replication-essential gene function of the E4 region (denoted an E1/E4-deficient adenoviral vector). An adenoviral vector deleted of the entire E4 region can elicit a lower host immune response.

Alternatively, the Ad vector lacks replication-essential gene functions in all or part of the E1 region and all or part of the E2 region (denoted an E1/E2-deficient adenoviral vector). Ad vectors lacking replication-essential gene functions in all or part of the E1 region, all or part of the E2 region, and all or part of the E3 region also are contemplated herein. If the Ad vector is deficient in a replication-essential gene function of the E2A region, the vector preferably does not comprise a complete deletion of the E2A region, which is less than about 230 base pairs in length. Generally, the E2A region of the adenovirus codes for a DBP (DNA binding protein), a polypeptide required for DNA replication. DBP is composed of 473 to 529 amino acids depending on the viral serotype. It is believed that DBP is an asymmetric protein that exists as a prolate ellipsoid consisting of a globular Ct with an extended Nt domain. Studies indicate that the Ct domain is responsible for DBP's ability to bind to nucleic acids, bind to zinc, and function in DNA synthesis at the level of DNA chain elongation. However, the Nt domain is believed to function in late gene expression at both transcriptional and post-transcriptional levels, is responsible for efficient nuclear localization of the protein, and also may be involved in enhancement of its own expression. Deletions in the Nt domain between amino acids 2 to 38 have indicated that this region is important for DBP function (Brough et al., *Virology*, 196, 269-281 (1993)). While deletions in the E2A region coding for the Ct region of the DBP have no effect on viral replication, deletions in the E2A region which code for amino acids 2 to 38 of the Nt domain of the DBP impair viral replication. It is preferable that the multiply replication-deficient adenoviral vector contain this portion of the E2A region of the adenoviral genome. In particular, for example, the desired portion of the E2A region to be retained is that portion of the E2A region of the adenoviral genome which is defined by the 5' end of the E2A region, specifically positions Ad5(23816) to Ad5(24032) of the E2A region of the adenoviral genome of serotype Ad5.

The Ad vector can be deficient in replication-essential gene functions of only the early regions of the adenoviral genome, only the late regions of the adenoviral genome, and both the early and late regions of the adenoviral genome. The adenoviral vector also can have essentially the entire adenoviral genome removed, in which case it is preferred that at least either the viral (i.e., adenoviral) inverted terminal repeats (Ad ITRs) and one or more promoters or the Ad ITRs and a packaging signal are left intact (i.e., an adenoviral amplicon). The larger the region of the adenoviral genome that is removed, the larger the piece of exogenous nucleic acid sequence that can be inserted into the genome. For example, given that the adenoviral genome is 36 kb, by leaving the Ad ITRs and one or more promoters intact, the exogenous insert capacity of the adenovirus is approximately 35 kb. Alternatively, a multiply deficient Ad vector that contains only an Ad ITR and a packaging signal effectively allows insertion of an exogenous nucleic acid sequence of approximately 37-38 kb. Of course, the inclusion of a spacer element in any or all of the deficient adenoviral regions will decrease the capacity of the adenoviral vector for large inserts. Suitable replication-deficient Ad vectors, including multiply deficient Ad vectors, are disclosed in U.S. Pat. Nos. 5,851,806 and 5,994,106 and International Patent Applications WO 95/34671 and WO 97/21826. An especially preferred adenoviral vector for use in the invention is that described in International Patent Application WO 02/00906.

It should be appreciated that the deletion of different regions of the Ad vector can alter the immune response of a mammal exposed to the Ad vector. In particular, the deletion of different regions can reduce the inflammatory response generated by the Ad vector. Furthermore, the Ad vector's coat protein can be modified so as to decrease the Ad vector's ability or inability to be recognized by a neutralizing antibody directed against the wild-type coat protein, as described in International Patent Application WO 98/40509.

The adenoviral vector, when multiply replication-deficient, especially in replication-essential gene functions of the E1 and E4 regions, preferably includes a spacer element to provide viral growth in a complementing cell line similar to that achieved by singly replication deficient Ad vectors, particularly an Ad vector comprising a deficiency in the E4 region. A spacer sequence is defined in the invention as any sequence of sufficient length to restore the size of the adenoviral genome to approximately the size of a wild-type adenoviral genome, such that the Ad vector is efficiently packaged into viral particles. The spacer element can contain any sequence or sequences which are of the desired length. The spacer element sequence can be coding or non-coding and native or non-native with respect to the adenoviral genome, but does not restore the replication-essential function to the deficient region. The spacer can be of any suitable size, desirably at least about 15 base pairs (e.g., between about 15 base pairs and about 12,000 base pairs), preferably about 100 base pairs to about 10,000 base pairs, more preferably about 500 base pairs to about 8,000 base pairs, even more preferably about 1,500 base pairs to about 6,000 base pairs, and most preferably about 2,000 to about 3,000 base pairs. The size of the spacer is limited only by the size of the insert that the Ad vector will accommodate (e.g., approximately 38 kb). In the absence of a spacer, production of fiber protein and/or viral growth of the multiply replication-deficient Ad vector is reduced by comparison to that of a singly replication-deficient Ad vector. However, inclusion of the spacer in at least one of the deficient adenoviral regions, preferably the E4 region, can counteract this decrease in fiber protein production and viral growth. The use of a spacer in an Ad vector is described in U.S. Pat. No. 5,851,806.

The Ad vector preferably contains a packaging domain. The packaging domain can be located at any position in the adenoviral genome, so long as the adenoviral genome is packaged into adenoviral particles. Preferably, the packaging domain is located downstream of the E1 region. More preferably, the packaging domain is located downstream of the E4 region. In a particularly preferred embodiment, the replication-deficient Ad vector lacks all or part of the E1 region and the E4 region. In this preferred embodiment, a spacer is inserted into the E4 region, a desired exogenous nucleic acid sequence of interest (e.g., a nucleic acid sequence encoding TNF-α) is located in the E1 region, and the packaging domain is located downstream of the E4 region. By relocating the packaging domain, the amount of potential overlap between the Ad vector and the cellular/helper virus genome used to propagate the Ad vector is reduced so as to reduce the probability of obtaining a replication-competent Ad vector.

The coat proteins of the Ad vector can be manipulated to alter the binding specificity of the resulting adenoviral particle. Suitable modifications to the coat proteins include, but are not limited to, insertions, deletions, or replacements in the adenoviral fiber, penton, pIX, pIIIa, pVI, or hexon proteins, or any suitable combination thereof, including insertions of various native or non-native ligands into portions of such coat proteins. Examples of Ad vectors with modified binding specificity are described in, e.g., U.S. Pat. Nos. 5,871,727, 5,885,808, and 5,922,315. Preferred modified Ad vector particles include those described in, for example, Wickham et al., *J. Virol.*, 71(10), 7663-9 (1997), Cripe et al., *Cancer Res.*, 61(7), 2953-60 (2001), van Deutekom et al., *J. Gene Med.*, 1(6), 393-9 (1999), McDonald et al., *J. Gene Med.*, 1(2), 103-10 (1999), Staba et al., *Cancer Gene Ther.*, 7(1), 13-9 (2000), Wickham, *Gene Ther.*, 7(2), 110-4 (2000), Kibbe et al., *Arch. Surg.*, 135(2), 191-7 (2000), Harari et al., *Gene Ther.*, 6(5), 801-7 (2000), Bouri et al., *Hum Gene Ther.*, 10(10), 1633-40 (1999), Wickham et al., *Nat. Biotechnol.*, 14(11), 1570-3 (1996), Wickham et al., *Cancer Immunol. Immunother.*, 45(3-4), 149-51 (1997), and Wickham et al., *Gene Ther.*, 2(10), 750-6 (1995), and U.S. Pat. Nos. 5,559,099; 5,712,136; 5,731,190; 5,770,442; 5,801,030; 5,846,782; 5,962,311; 5,965,541; 6,057,155; 6,127,525; and 6,153,435; and International Patent Applications WO 96/07734, WO 96/26281, WO 97/20051, WO 98/07865, WO 98/07877, WO 98/40509, WO 98/54346, WO 00/15823, and WO 01/58940.

Replication-deficient Ad vectors are typically produced in complementing cell lines that provide gene functions not present in the replication-deficient Ad vectors, but required for viral propagation, at appropriate levels in order to generate high titers of viral vector stock. A preferred cell line complements for at least one and preferably all replication-essential gene functions not present in a replication-deficient adenovirus. The complementing cell line can complement for a deficiency in at least one replication-essential gene function encoded by the early regions, late regions, viral packaging regions, virus-associated RNA regions, or combinations thereof, including all adenoviral functions (e.g., to enable propagation of adenoviral amplicons, which comprise minimal adenoviral sequences, such as only Ad ITRs and the packaging signal or only Ad ITRs and an adenoviral promoter). Most preferably, the complementing cell line complements for a deficiency in at least one replication-essential gene function (e.g., two or more replication-essential gene functions) of the E1 region of the adenoviral genome, particularly a deficiency in a replication-essential gene function of each of the E1A and E1B regions. In addition, the complementing cell line can complement for a deficiency in at least one replication-essential gene function of the E2 (particularly as concerns the adenoviral DNA polymerase and terminal protein) and/or E4 regions of the adenoviral genome. Desirably, a cell that complements for a deficiency in the E4 region comprises the E4-ORF6 gene sequence and produces the E4-ORF6 protein. Such a cell desirably comprises at least ORF6 and no other ORF of the E4 region of the adenoviral genome. The cell line preferably is further characterized in that it contains the complementing genes in a non-overlapping fashion with the adenoviral vector, which minimizes, and practically eliminates, the possibility of the vector genome recombining with the cellular DNA. Accordingly, the presence of replication-competent adenoviruses (RCA) is minimized if not avoided in the vector stock, which, therefore, is suitable for certain therapeutic purposes, especially gene therapy purposes. The lack of RCA in the vector stock avoids the replication of the Ad vector in non-complementing cells. The construction of complementing cell lines involves standard molecular biology and cell culture techniques, such as those described by Sambrook et al. (1989), supra, and Ausubel et al. (1984), supra. Complementing cell lines for producing adenoviral vectors include, but are not limited to, 293 cells (described in, e.g., Graham et al., *J. Gen. Virol.*, 36, 59-72 (1977)), PER.C6 cells (described in, e.g., International Patent Application WO 97/00326, and U.S. Pat. Nos. 5,994,128 and 6,033,908), and 293-ORF6 cells (described in, e.g., International Patent Application WO 95/34671 and Brough et al., *J. Virol.*, 71, 9206-9213 (1997)).

The selection of an expression construct for use in the invention will depend on a variety of factors such as, for example, the host, immunogenicity of the expression construct, the desired duration of protein production, the target cell, and the like. As each type of expression construct has distinct properties, a researcher has the freedom to tailor the invention to any particular situation. Moreover, more than one type of expression construct can be used, if desired.

According to the invention, the nucleic acid molecule of the invention is operably linked to regulatory sequences necessary for expression, especially a promoter. A "promoter" is a DNA sequence that directs the binding of RNA polymerase and thereby promotes RNA synthesis. A nucleic acid sequence is "operably linked" to a promoter when the promoter is capable of directing transcription of that nucleic acid sequence. A promoter can be native or non-native to the nucleic acid sequence to which it is operably linked.

Any promoter (i.e., whether isolated from nature or produced by recombinant DNA or synthetic techniques) can be used in connection with the invention to provide for transcription of a particular nucleic acid sequence. The promoter preferably is capable of directing transcription in a eukaryotic (desirably mammalian) cell. The functioning of the promoter can be altered by the presence of one or more enhancers and/or silencers present on the vector. "Enhancers" are cis-acting elements of DNA that stimulate or inhibit transcription of adjacent genes. An enhancer that inhibits transcription also is termed a "silencer." Enhancers differ from DNA-binding sites for sequence-specific DNA binding proteins found only in the promoter (which also are termed "promoter elements") in that enhancers can function in either orientation, and over distances of up to several kilobase pairs (kb), even from a position downstream of a transcribed region.

The invention preferentially employs a viral promoter. Suitable viral promoters are known in the art and include, for instance, cytomegalovirus (CMV) promoters, such as the CMV immediate-early promoter, promoters derived from human immunodeficiency virus (HIV), such as the HIV long terminal repeat promoter, Rous sarcoma virus (RSV) promoters, such as the RSV long terminal repeat, mouse mammary tumor virus (MMTV) promoters, HSV promoters, such as the Lap2 promoter or the herpes thymidine kinase promoter (Wagner et al., *PNAS*, 78, 144-145 (1981)), promoters derived from SV40 or Epstein Barr virus, an adeno-associated viral promoter, such as the p5 promoter, and the like. Preferably, the viral promoter is an adenoviral promoter, such as the Ad2 or Ad5 major late promoter and tripartite leader, a CMV promoter, or an RSV promoter.

Many of the above-described promoters are constitutive promoters. Instead of being a constitutive promoter, the promoter can be an inducible promoter, i.e., a promoter that is up- and/or down-regulated in response to appropriate signals. Examples of suitable inducible promoter systems include, but are not limited to, the IL-8 promoter, the metallothionine inducible promoter system, the bacterial lacZYA expression system, the tetracycline expression system, and the T7 polymerase system. Further, promoters that are selectively activated at different developmental stages (e.g., globin genes are differentially transcribed from globin-associated promoters in embryos and adults) can be employed. The promoter sequence that regulates expression of the nucleic acid sequence can contain at least one heterologous regulatory sequence responsive to regulation by an exogenous agent. The regulatory sequences are preferably responsive to exogenous agents such as, but not limited to, drugs, hormones, or other gene products. For example, the regulatory sequences, e.g., promoter, preferably are responsive to glucocorticoid receptor-hormone complexes, which, in turn, enhance the level of transcription of a therapeutic peptide or a therapeutic fragment thereof.

One of ordinary skill in the art will appreciate that each promoter drives transcription, and, therefore, protein expression, differently with respect to the time and amount of protein produced. For example, the CMV promoter is characterized as having peak activity shortly after transduction, i.e., about 24 hours after transduction, then quickly tapering off. On the other hand, the RSV promoter's activity increases gradually, reaching peak activity several days after transduction, and maintains a high level of activity for several weeks. Indeed, sustained expression driven by an RSV promoter has been observed in all cell types studied, including, for instance, liver cells, lung cells, spleen cells, diaphragm cells, skeletal muscle cells, and cardiac muscle cells. Thus, a promoter can be selected for use in the invention by matching its particular pattern of activity with the desired pattern and level of expression of a nucleic acid sequence of interest. Alternatively, a hybrid promoter can be constructed which combines the desirable aspects of multiple promoters. For example, a CMV-RSV hybrid promoter combining the CMV promoter's initial rush of activity with the RSV promoter's high maintenance level of activity would be especially preferred for use in many embodiments of the invention. It is also possible to select a promoter with an expression profile that can be manipulated by an investigator.

A nucleic acid sequence encoding a marker protein, such as green fluorescent protein or luciferase, also can be present in the expression construct. Such marker proteins are useful in construction of the expression construct as well as in determining expression construct migration if administered to an organism. Marker proteins also can be used to determine points of injection in order to efficiently space injections of an expression construct composition to provide a widespread area of treatment, if desired. Alternatively, a nucleic acid sequence encoding a selection factor, which also is useful in vector construction protocols, can be part of the expression construct.

Negative selection genes can be incorporated into any of the above-described expression constructs. A preferred embodiment is an HSV tk gene cassette (Zjilstra et al., *Nature*, 342, 435 (1989); Mansour et al., *Nature*, 336, 348 (1988); Johnson et al., *Science*, 245, 1234 (1989): Adair et al., *PNAS*, 86, 4574 (1989); Capecchi, *Science*, 244, 1288 (1989)) operably linked to the E2 promoter. The tk expression cassette (or other negative selection expression cassette) is inserted into an adenoviral genome, for example, as a replacement for a substantial deletion of the E3 gene. Other negative selection genes will be apparent to those of skill in the art.

With respect to promoters, nucleic acid sequences, selectable markers, and the like, located on an expression construct according to the invention, such elements can be present as part of a cassette, either independently or coupled. In the context of the invention, a "cassette" is a particular base sequence that possesses functions, which facilitate subcloning, and recovery of nucleic acid sequences (e.g., one or more restriction sites) or expression (e.g., polyadenylation or splice sites) of particular nucleic acid sequences.

Construction of a nucleic acid sequence operably linked to regulatory sequences necessary for expression is well within the skill of the art (see, for example, Sambrook et al. (1989), supra). With respect to the expression of nucleic acid sequences according to the invention, the ordinary skilled artisan is aware that different genetic signals and processing events control levels of nucleic acids and proteins/peptides in a cell, such as, for instance, transcription, mRNA translation, and post-transcriptional processing. Transcription of DNA into RNA requires a functional promoter, as described herein.

Protein expression is dependent on the level of RNA transcription that is regulated by DNA signals, and the levels of DNA template. Similarly, translation of mRNA requires, at the very least, an AUG initiation codon, which is usually located within 10 to 100 nucleotides of the 5' end of the message. Sequences flanking the AUG initiator codon have been shown to influence its recognition by eukaryotic ribosomes, with conformity to a perfect Kozak consensus sequence resulting in optimal translation (see, e.g., Kozak, *J. Mol. Biol.*, 196, 947-950 (1987)). Also, successful expression of an exogenous nucleic acid in a cell can require post-translational modification of a resultant protein. Thus, production of a protein can be affected by the efficiency with which DNA (or RNA) is transcribed into mRNA, the efficiency with which mRNA is translated into protein, and the ability of the cell to carry out post-translational modification. These are all factors of which the ordinary skilled artisan is aware and is capable of manipulating using standard means to achieve the desired end result.

Along these lines, to optimize protein production, preferably the nucleic acid molecule of the invention further comprises a polyadenylation site following the coding region of the nucleic acid sequence. Also, preferably all the proper transcription signals (and translation signals, where appropriate) will be correctly arranged such that the nucleic acid sequence will be properly expressed in the cells into which it is introduced. Moreover, if the nucleic acid sequence encodes a protein or peptide, which is a processed or secreted protein or acts intracellularly, preferably the nucleic acid sequence further comprises the appropriate sequences for processing, secretion, intracellular localization, and the like.

It will be appreciated that the expression construct can comprise multiple nucleic acid molecules of the invention. For example, the expression construct can comprise multiple copies of a nucleic acid molecule of the invention, each copy operably linked to a different promoter or to identical promoters. Moreover, any nucleic acid molecule described herein can be altered from its native form to increase or decrease a desired effect (e.g., to increase its therapeutic effect). For example, a cytoplasmic form of a nucleic acid molecule can be converted to a secreted form by incorporating a signal peptide into the encoded gene product.

The invention further provides a cell (i.e., a host cell) comprising an isolated or purified nucleic acid molecule or an expression construct as described herein. Examples of host cells include, but are not limited to, a prokaryotic or eukaryotic host cell. Prokaryotic cells include those derived from *E. coli, B. subtilis, P. aerugenosa, S. cerevisiae*, and *N. crassa*. Preferably, the host cell is derived from a mammal, such as a human.

A nucleic acid molecule or, preferably, an expression construct, of the invention desirably is formulated and administered to a mammal in a composition. Such a composition typically comprises a nucleic acid molecule or an expression construct of the invention along with a carrier. Preferably, the carrier is a pharmaceutically (e.g., physiologically) acceptable carrier and can be used within the context of the invention. Such carriers are well known in the art. The choice of carrier will be determined, in part, by the particular site to which the composition is to be administered and the particular method used to administer the adenoviral vector composition.

Suitable formulations include aqueous and non-aqueous solutions, isotonic sterile solutions, which can contain antioxidants, buffers, bacteriostats, and solutes that render the formulation isotonic with the blood or intraocular fluid of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, immediately prior to use. Extemporaneous solutions and suspensions can be prepared from sterile powders, granules, and tablets of the kind previously described. When administering a composition, preferably the pharmaceutically acceptable carrier is a buffered saline solution. More preferably, the composition for use in the invention is administered in a composition formulated to protect the nucleic acid molecule or expression construct from damage prior to administration. For example, the composition can be formulated to reduce loss of the nucleic acid molecule or expression construct on devices used to prepare, store, or administer the composition, such as glassware, syringes, or needles. The composition can be formulated to decrease the light sensitivity and/or temperature sensitivity of the expression construct itself. To this end, the composition preferably comprises a pharmaceutically acceptable liquid carrier, such as, for example, those described above, and a stabilizing agent selected from the group consisting of polysorbate 80, L-arginine, polyvinylpyrrolidone, trehalose, and combinations thereof (see, e.g., U.S. Pat. No. 6,225,289). The use of such a composition will extend the shelf life of the composition, facilitate administration, and increase the effectiveness of the nucleic acid molecule or expression construct. In this regard, the composition also can be formulated to enhance transduction efficiency.

In addition, the composition of the invention can comprise, or alternatively can be co-administered with, other therapeutic or biologically active agents. By "co-administration" is meant administration before, concurrently with, e.g., in combination with the composition in the same formulation or in separate formulations, or after administration of the composition as described above. For example, nucleic acid sequences, proteins, and/or other agents useful in the treatment of a particular pathologic state can be present of co-administered with the composition of the invention. Suitable biologically active agents can include, for example, factors that control inflammation, such as ibuprofen or steroids, which can be co-administered to reduce swelling and inflammation associated with administration of the composition. Immunosuppressive agents can be co-administered to reduce inappropriate immune responses related to a disorder or the practice of the inventive method. Anti-angiogenic factors, such as soluble growth factor receptors, growth factor antagonists, e.g., angiotensin, and the like also can be co-administered, as well as can be neurotrophic factors. Similarly, vitamins and minerals, antioxidants, and micronutrients can be co-administered. Antibiotics, e.g., microbicides and fungicides, can be co-administered to reduce the risk of infection associated with a particular pathologic state.

A nucleic acid molecule of the invention, and, preferably, an expression construct of the invention, can be useful to prophylactically or therapeutically treat a mammal for a pathologic state. Such treatment will involve the administration of a composition of the invention to a mammal. Preferably, such treatment will involve the administration of an expression construct of the invention (e.g., an expression construct composition) to a mammal. In such instances, the nucleic acid molecule, whether or not present in an expression construct, encodes a therapeutic factor. Preferably the therapeutic factor is an angiogenic factor, such as VEGF. Other suitable therapeutic factors will be apparent to those skilled in the art and can include, for example, fibroblast growth factor, fibroblast growth factor 3, fibroblast growth factor 8, VEGF B, VEGF D, hypoxia-inducible factor 1α, hepatocyte growth factor, and platelet derived growth factors. Upon administration, the nucleic acid molecule of the invention is expressed, resulting in the subsequent production of the therapeutic factor. In the context of the invention, such expression and subsequent production of the therapeutic factor allows for the production of one isoform of the gene as compared to another isoform. This selective isoform production is useful to prophylactically or therapeutically treat the mammal for the pathologic state. In one aspect of the invention, the nucleic acid molecule can be constructed by manipulating the splice donor, branch point, and/or splice acceptor regions, as described above. For example, a nucleic acid molecule, as set forth in FIG. 1, can be included in an expression construct and administered to a mammal to promote the production of VEGF189 at the expense of VEGF165. Such an effect is desirable when the angiogenic signal provided by VEGF189 is more potent than that provided by VEGF165, or the safety of VEGF189 is greater than that provided by VEGF165. The production of VEGF189 also can be at the expense of production of VEGF121, in addition or in alternative to a decrease in VEGF165 production.

By "prophylactic" is meant the protection, in whole or in part, against a pathologic state. By "therapeutic" is meant the amelioration, in whole or in part, of the pathologic state, itself, and/or the protection, in whole or in part, against further progression of the disease. One of ordinary skill in the art will appreciate that any degree of protection from, or amelioration of, a pathologic state is beneficial to a patient.

When used for therapeutic purposes, the nucleic acid molecule or expression construct of the invention can be purified from a host cell using a variety of conventional purification methods, such as CsCl gradients or chromatography (e.g., ion-exchange chromatography). Such purification techniques are well known and frequently practiced in the art.

The pathologic state can be any pathologic state. For example, the pathologic state can be a disorder caused by an increased or decreased level of a particular gene product(s). By "increased level" is meant a level above that which is considered normal. Similarly, by "decreased level" is meant a level below that which is considered normal. Many angiogenic-related diseases result from an increased or a decreased level of a particular isoform of a gene. Accordingly, the pathologic state preferably is an angiogenic-related disease, and the nucleic acid sequence preferably encodes an angiogenic factor, which promotes the production of new blood vessels.

The pathologic state can be any type of disease that can receive benefit from the growth of new blood vessels. For example, the pathologic state can be all forms of atherosclerosis (e.g., coronary artery disease), peripheral vascular disease and diffuse atherosclerosis, wound healing, tissue repair and remodeling following surgery, and congestive heart failure.

Other pathologic states also are contemplated in the context of the invention. For example, the pathologic state can be an inflammatory disease (e.g., arthritis), a neurodegenerative disease, a disease of an organ which is attributed to the presence of the increased or decreased level of a particular isoform(s), or any other pathologic state for which the modulation of different isoforms of a gene associated with a pathologic state will treat or prevent the pathologic state.

Suitable methods, both invasive and noninvasive methods, of directly administering the composition are available. Although more than one route can be used for administration, a particular route can provide a more immediate and more effective reaction than another route. The inventive method is not dependent on the mode of administering the composition to a mammal, preferably a human, to achieve the desired effect. As such, any route of administration is appropriate so long as the nucleic acid molecule is processed through RNA splicing as described herein. The composition can be appropriately formulated and administered in the form of a local injection, lotion, ointment, implant, or the like. The composition can be applied, for example, topically. The composition can be administered through multiple applications and/or multiple routes to ensure sufficient exposure of cells to the composition.

The nucleic acid molecule or expression construct comprising the nucleic acid molecule is preferably formulated into a composition prior to administration and is administered as soon as possible after it has been determined that an animal, such as a mammal, specifically a human, is at risk for a particular pathologic state (prophylactic treatment) or has developed the pathologic state (therapeutic treatment). Treatment will depend, in part, upon the particular therapeutic factor expressed from the nucleic acid sequence, the route of administration, and the cause and extent, if any, of the pathologic state.

The composition can be administered using invasive procedures, such as, for instance, local injection to a target tissue (e.g., intramuscular injection). Local injections typically involve the administration of the composition by a catheter or similar device inserted sufficiently deeply into the proximal portion of the organ- or tissue-feeding artery or arteries so that gene transfer is effected substantially only into the cells of the target organ or tissue. Pharmaceutically acceptable carriers for injectable compositions are well known to those of ordinary skill in the art (see Pharmaceutics and Pharmacy Practice, J. B. Lippincott Co., Philadelphia, Pa., Banker and Chalmers, eds., pages 238-250 (1982), and ASHP Handbook on Injectable Drugs, Toissel, 4th ed., pages 622-630 (1986)).

The composition can be non-invasively administered to a mammal. For instance, if multiple surgeries have been performed, the mammal displays low tolerance to anesthetic, or other disorders exist, topical administration of the composition may be most appropriate. Topical formulations are well known to those of skill in the art. A composition also can be administered non-invasively using a needleless injection device, such as the Biojector 2000 Needle-Free Injection Management System® available from Bioject, Inc.

The composition is preferably present in or on a device that allows controlled or sustained release, such as a biocompatible polymeric matrix, meshwork, mechanical reservoir, or mechanical implant. Implants (see, e.g., U.S. Pat. Nos. 5,443,505, 4,853,224, and 4,997,652) and devices (see, e.g., U.S. Pat. Nos. 5,554,187, 4,863,457, 5,098,443, and 5,725,493), such as an implantable device, e.g., a mechanical reservoir or an implant or a device comprised of a polymeric composition, are particularly useful for the administration of the composition. The composition also can be administered in the form of a sustained-release formulation (see, e.g., U.S. Pat. No. 5,378,475) comprising, for example, gelatin, chondroitin sulfate, a polyphosphoester, such as bis-2-hydroxyethyl-terephthalate (BHET), or a poly-lactic-glycolic acid.

When administering the composition, the appropriate dosage and route of administration can be selected to minimize loss of the nucleic acid molecule or expression construct or inactivation of the either of the foregoing due to a host's immune system. For example, for in vivo administration, it can be advantageous to administer, to a mammal being treated, an immunosuppressive agent (e.g., cyclophosphamide or FK506) or monoclonal antibody that can block a T cell receptor, prior to performing the inventive method. Prior administration of an immunosuppressive agent or monoclonal antibody can serve to decrease the amount of composition cleared by the immune system of the mammal.

When practiced in vivo, any suitable organs or tissues or component cells can be targeted for delivery. Preferably, the organs/tissues/cells employed are of the circulatory system (i.e., heart, blood vessels or blood), respiratory system (i.e., nose, pharynx, larynx, trachea, bronchi, bronchioles, lungs), gastrointestinal system (i.e., mouth, pharynx, esophagus, stomach, intestines, salivary glands, pancreas, liver, gallbladder), urinary system (i.e., kidneys, ureters, urinary bladder, urethra), nervous system (i.e., brain and spinal cord, and special sense organs such as the eye), and integumentary system (i.e., skin). Even more preferably, the cells being targeted are selected from the group consisting of heart, blood vessel, lung, liver, gallbladder, urinary bladder, and eye cells.

The dose of composition administered to a mammal, particularly a human, in accordance with the invention should be in an amount sufficient to treat prophylactically or therapeutically a mammal for a pathologic state. Dosage will depend upon a variety of factors, including the age, species, the pathology in question, and condition or disease state. Dosage also depends on the nucleic acid sequences contained in an expression construct, as well as the amount of tissue about to be affected or actually affected by the disease. The size of the dose also will be determined by the route, timing, and frequency of administration as well as the existence, nature, and extent of any adverse side effects that might accompany the administration of a particular composition and the desired physiological effect. It will be appreciated by one of ordinary skill in the art that various conditions or disease states, in particular, chronic conditions or disease states, may require prolonged treatment involving multiple administrations.

Suitable doses and dosage regimens can be determined by conventional range-finding techniques known to those of ordinary skill in the art. When administering an expression construct, such as a viral vector, preferably about $10^6$ viral particles to about $10^{12}$ viral particles are delivered to the diseased tissue. In other words, a composition of the expression construct can be administered that comprises an expression construct concentration of about $10^6$ particles/ml to about $10^{12}$ particles/ml (including all integers within the range of about $10^6$ particles/ml to about $10^{12}$ particles/ml), preferably about $10^{10}$ particles/ml to about $10^{12}$ particles/ml. Typically, about 0.1 µl to about 100 µl of such an expression construct composition to each affected tissue. Of course, other routes of administration may require smaller or larger doses to achieve a therapeutic effect. Any necessary variations in dosages and routes of administration can be determined by the ordinarily skilled artisan using routine techniques known in the art.

In some embodiments, it is advantageous to administer two or more (i.e., multiple) doses of the composition. The invention provides for multiple applications of the composition in order to achieve sufficient integration, thereby prophylactically or therapeutically treating a particular disease state. For example, at least two applications of a composition can be administered to the same tissue. Preferably, the targeted cells are contacted with two applications or more of the composition via direct administration to the desired tissue within about 30 days or more. More preferably, two or more applications are administered to cells of the same tissue within about 90 days or more. However, three, four, five, six, or more doses can be administered in any time frame (e.g., 2, 7, 10, 14, 21, 28, 35, 42, 49, 56, 63, 70, 77, 85 or more days between doses) so long as the desired prophylactic or therapeutic effect is achieved.

The composition can be introduced ex vivo into cells, previously removed from the mammal, especially a human, and exposed to the composition, although this is less preferred. Such transduced autologous or homologous host cells, reintroduced into the mammal (e.g., human), will express directly the nucleic acid sequences contained therein in vivo following initiation of DNA replication. One ex vivo therapeutic option involves the encapsidation of infected cells into a biocompatible capsule, which can be implanted into a particular tissue. Such cells need not be isolated from the patient, but instead can be isolated from another individual and implanted into the patient.

The administration of a composition of the invention will desirably promote the production of one isoform of a particular gene at the expense of another isoform. Such a change in production levels will then be responsible for treating a pathologic state as described above. In this respect, the invention also provides a method of assessing the effectiveness of treatment of a pathologic state in a mammal, wherein a desired isoform of a particular gene is a marker for the pathologic state. Such a method will involve measuring the level of the isoform in a test sample obtained from the mammal, wherein the level of the isoform in the test sample is indicative of the effectiveness of the treatment of the cancer in the mammal. The level of the isoform in the test sample can be measured by comparing the level of the isoform in the test sample to the level of the isoform in another test sample obtained from the mammal over time. Depending on which gene the isoform is produced from and which pathologic state is being assessed, an increase, a decrease, or no change in the level of the isoform from one sample to the next can be indicative of the treatment being either effective or ineffective. The determination of the appropriate level of a particular isoform and whether or not an increase, a decrease, or no change in the level of the isoform is detected and indicative of the effectiveness of treatment for a particular pathologic state will be apparent to one skilled in the art, and will depend, generally, on the gene the isoform is derived from as well as the pathologic state for which it is associated with. For example, the level of VEGF189 or, alternatively, VEGF165 and/or VEGF121 can be measured over time. Either an increased level of VEGF189 or a decreased level of VEGF165 and/or VEGF121 will be indicative of the treatment being effective with the nucleic acid molecule or expression construct of the invention. Alternatively, a decreased level of VEGF189 or an increased level of VEGF165 and/or VEGF121 is indicative of the treatment being ineffective.

As used herein, the term "decreased level" can be defined as detecting a desired isoform in a test sample obtained from a mammal at a level below that which is considered normal. For example, the level of an isoform in a test sample is decreased when the mRNA encoding the isoform or a polypeptide molecule comprising an amino acid sequence encoding the isoform is detected at a level below that which is considered normal. Conversely, the term "increased level" can be defined as detecting a desired isoform in a test sample obtained from a mammal at a level above that which is considered normal. For example, the level of an isoform in a test sample is increased when the mRNA encoding the isoform or a polypeptide molecule comprising an amino acid sequence encoding the isoform is detected at a level above that which is considered normal. "Normal levels" pertain to an already determined range of the isoform, established from mammals which are free of the pathologic state of the same species, and are generally accepted and recognized in the art.

|  | Branch Point | Splice Acceptor | Splice Donor |
|---|---|---|---|
| Wild-type | CTTTTAC (SEQ ID NO:6) | GTTTTTTTATTTTCCAG/AAA (SEQ ID NO:8) | GT/GTACGT (SEQ ID NO:10) |
| Mutated | CACTGAC (SEQ ID NO:7) | GTTTTTTTTTTTCCAG/AAA (SEQ ID NO:9) | GT/GTAAGT (SEQ ID NO:11) |

The test sample used in conjunction with the invention can be any of those typically used in the art and will vary depending on the condition of the mammal (e.g., whether or not a pathologic state has developed in the mammal). For example, the test sample can be tissue, which tissue comprises somatic cells. Preferably, however, the test sample is one which can be obtained in the least invasive manner with respect to the mammal, such as a blood or serum sample.

The following examples serve to illustrate the present invention and are not intended to limit its scope in any way.

EXAMPLE 1

This example demonstrates the construction of a nucleic acid molecule of the invention.

The human VEGF gene was reconstructed as a hybrid using the cDNA for exons 1 through 5 joined to the genomic configuration for exons 6, 7, and 8 (including introns 5, 6, and 7). Exon 5 was mutated to contain a SacI restriction site, exon 6 was mutated to contain an XbaI restriction site, and exon 7 was mutated to contain an XhoI restriction site. A HindIII restriction site was created immediately following the stop codon of exon 8. The cloning and sequencing of the introns allowed the splicing signals for these introns to be identified.

The 189 amino acid isoform of VEGF includes the amino acids encoded by exon 6 which are excluded from the 165 amino acid form. Accordingly, mutations were made in each of the splice acceptor, branch point, and splice donor site of exon 6 to increase the production of VEGF189 at the expense of VEGF165. By making appropriate mutations by site-specific mutagenesis, the efficiency of recognition of exon 6 was enhanced.

These mutations are outlined in the table below. The "/" in the splice acceptor sequences represents the end of the splice acceptor sequence and the beginning of exon 6. Similarly, the "/" in the splice donor sequences represents the end of exon 6 and the beginning of the splice donor sequence. Mutations are indicated in bold.

The nucleic acid molecule of the invention can be used to increase the abundance of VEGF189 at the expense of VEGF165.

EXAMPLE 2

This example demonstrates the construction of a nucleic acid molecule of the invention.

The human VEGF gene was reconstructed as a hybrid using the cDNA for exons 1 through 5 joined to the genomic configuration for exons 6, 7, and 8 (including introns 5, 6, and 7). Exon 5 was mutated to contain a SacI restriction site, exon 6 was mutated to contain an XbaI restriction site, and exon 7 was mutated to contain an XhoI restriction site. A HindIII restriction site was created immediately following the stop codon of exon 8. The cloning and sequencing of the introns allowed the splicing signals for these introns to be identified.

Mutations were made in each of the splice acceptor, branch point, and splice donor site of exon 6A to produce two nucleic acid sequences which, when expressed, favor production of VEGF189 at the expense of VEGF121 compared to the splicing signals in the wild-type human VEGF gene.

|  | Branch Point | Splice Acceptor | Splice Donor |
|---|---|---|---|
| VEGF-ALL | ACCTTAC (SEQ ID NO:12) | TTTTTATTTCCAG/AAA (SEQ ID NO:14) | GT/GTACGT (SEQ ID NO:10) |
| VEGF-ALL6A+ | CCCTGAG (SEQ ID NO:13) | TTTTTCTTTCCAG/AAA (SEQ ID NO:15) | GT/GTAAGT (SEQ ID NO:11) |

The VEGF-ALL nucleic acid comprises a VEGF cDNA/genomic DNA hybrid containing native splicing signals which promotes production of all isoforms of VEGF by alternate splicing. The VEGF-ALL6A+ nucleic acid sequence contains splicing signals which promote the inclusion of exon 6A in the messenger RNA. The VEGF-ALL6A+ nucleic acid sequence produced a greater amount of VEGF189 and a decreased amount of VEGF121 as compared to that of the VEGF-ALL nucleic acid sequence as measured by Western Blot.

The activities of the products of the VEGF-ALL nucleic acid sequence and VEGF-ALL6A+ nucleic acid sequence were examined. The femoral artery of C58B1/6 mice was ligated to induce ischemia in the hindlimb (see, for example, U.S. Pat. No. 6,518,255). A dose ($1 \times 10^5$ particle units (pu)) of replication-deficient adenoviral vector comprising deletions in the E1 and E3 regions of the adenoviral genome and comprising either the VEGF-ALL nucleic acid sequence (AdVEGF-ALL) or the VEGF-ALL6A+ nucleic acid sequence (AdVEGF-ALL6A+) was injected into the hindlimb. Blood flow restoration to the hindlimb was quantified by a Doppler flowmeter at 3, 7, 14, 21, and 28 days post-administration of the adenoviral vector. The VEGF-ALL nucleic acid sequence and the VEGF-ALL6A+ nucleic acid sequence mediated similar, if not equivalent, blood flow restoration at each time point.

Expression of VEGF isoforms can cause edema and death of a host. Accordingly, safety parameters for each VEGF-encoding nucleic acid sequence were examined. C58B1/6 mice were intratracheally administered $5 \times 10^{10}$ pu of AdVEGF-ALL or AdVEGF-ALL6A+. Five days later, the mice were sacrificed and edema in the lung was evaluated as measured by the ratio of wet weight/dry weight of lung tissue. An increased level of pulmonary edema was observed in mice administered the VEGF-ALL nucleic acid sequence as compared to mice administered the VEGF-ALL6A+ nucleic acid sequence.

Overall survival of mice administered the VEGF-ALL nucleic acid sequence and the VEGF-ALL6A+ nucleic acid sequence also was determined. C58B1/6 mice were intravenously administered $5 \times 10^{10}$ pu of AdVEGF-ALL, AdVEGF-ALL6A+, or an E1,E3-deficient adenoviral vector lacking a transgene (AdNull). The survival rate of the mice over ten days post-administration of the adenoviral vectors was determined. All mice administered AdNull survived for ten days post-administration. The survival rate of mice administered AdVEGF-ALL decreased from 100% to 20% at day 3. At day 4, all of the mice had expired. Mice administered AdVEGF-ALL6A+ survived substantially longer than mice administered AdVEGF-ALL. The survival rate for mice administered AdVEGF-ALL6A+ decreased from 100% to 80% at day 6. Twenty percent of the mice survived until day 8. None of the mice administered AdVEGF-ALL6A+ survived beyond day 9.

This example demonstrates that a VEGF nucleic acid sequence can be manipulated to increase production of VEGF189 at the expense of VEGF121 while retaining activity of the gene products and minimizing undesired characteristics attributed to VEGF production.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An isolated or purified nucleic acid molecule comprising SEQ ID NO:1.

2. An expression construct comprising the isolated or purified nucleic acid molecule of claim 1.

3. The expression construct of claim 2, wherein the expression construct is a viral vector.

4. The expression construct of claim 3, wherein the expression construct is an adenoviral vector.

5. The expression construct of claim 4, wherein the adenoviral vector is deficient in one or more replication-essential gene functions.

6. A composition comprising the isolated or purified nucleic acid molecule of claim 1 and a carrier.

7. A composition comprising the expression construct of claim 2.

8. An isolated cell comprising the expression construct of claim 2.

* * * * *